US00PP11863P2

(12) United States Plant Patent
Rother

(10) Patent No.: US PP11,863 P2
(45) Date of Patent: May 8, 2001

(54) OSTEOSPERMUM PLANT NAMED 'WHITE MOON'

(76) Inventor: Reinhard W. Rother, 56 Emerald Monbulk Road, Emerald, Victoria, 3782 (AU)

( * ) Notice: Subject to any disclaimer, the term of this patent is extended or adjusted under 35 U.S.C. 154(b) by 0 days.

(21) Appl. No.: 09/257,096

(22) Filed: Feb. 22, 1999

(51) Int. Cl.[7] ..... A01H 5/00

(52) U.S. Cl. ..... Plt./360

(58) Field of Search ..... Plt./360

(56) References Cited

PUBLICATIONS

Huxley, A., Griffiths, M., and Levy, M.. The New Royal Horticultural Society Dictionary of Gardening. Vol. 3. p. 416, Jul. 10, 1992.*

* cited by examiner

*Primary Examiner*—Bruce R. Campell
*Assistant Examiner*—Michelle Kizilkata
(74) *Attorney, Agent, or Firm*—C. A. Whealy

(57) ABSTRACT

A distinct cultivar of Osteospermum plant named 'White Moon', characterized by its upright, mounding and outwardly spreading growth habit; small numerous leaves and large upright inflorescences on long peduncles; vigor; freely branching habit; white-colored ray florets contrasted by dark bluish purple-tipped disc florets and bluish base of ray florets; and numerous inflorescences per plant.

1 Drawing Sheet

BACKGROUND OF THE INVENTION

The present invention relates to a new and distinct cultivar of Osteospermum plant, botanically known as *Osteospermum ecklonis* and referred to by the cultivar name 'White Moon'.

The new cultivar is a product of a planned breeding program conducted by the Inventor in Emerald, Victoria, Australia. The objective of the breeding program was to create new compact Osteospermum cultivars with large flowers.

The new cultivar originated from a cross made by the Inventor in 1993 of a proprietary selection of *Osteospermum ecklonis* identified as 90/75 as the female, or seed, parent and the *Osteospermum ecklonis* cultivar Sparkler II, not patented, as the male, or pollen, parent. The new Osteospermum was selected by the Inventor as a flowering plant within the progeny of this cross in a controlled environment in Emerald, Victoria, Australia in 1993.

Plants of the new cultivar are different from plants of the female parent, the selection 90/75 in leaf shape, peduncle length and inflorescence size. Plants of the new Osteospermum are more compact than plants of the male parent, the cultivar Sparkler II.

Asexual propagation of the new cultivar by terminal cuttings and by tissue culture at Emerald, Victoria, Australia, has shown that the unique features of this new Osteospermum are stable and reproduced true to type in successive generations.

SUMMARY OF THE INVENTION

The following traits have been repeatedly observed and are determined to be the unique characteristics of 'White Moon'. These characteristics in combination distinguish 'White Moon' as a new and distinct cultivar:

1. Upright, mounding and outwardly spreading growth habit.

2. Small numerous leaves and large upright inflorescences on long peduncles.
3. Vigorous and freely branching.
4. White-colored ray florets contrasted by dark bluish purple-tipped disc florets and bluish base of ray florets.
5. Numerous inflorescences per plant.

The new cultivar can be compared to the Osteospermum cultivar Sparkler, not patented. However in side-by-side comparisons conducted in Emerald, Victoria, Australia, plants of the new cultivar are more compact and differ in leaf shape, inflorescence size and peduncle length.

The cultivar 'White Moon' has not been observed under all possible environmental conditions. The phenotype may vary somewhat with variations in environment such as temperature, daylength and light intensity, without, however, any variance in genotype.

BRIEF DESCRIPTION OF THE PHOTOGRAPHS

The accompanying colored photographs illustrate the overall appearance of the new cultivar, showing the colors as true as it is reasonably possible to obtain in colored reproductions of this type.

The photograph at the top of the sheet comprises a top perspective view of a typical flowering plant of 'White Moon'.

The photograph at the bottom of the sheet is a close-up view of lower and upper surfaces of typical inflorescences (top) and upper and lower surfaces of typical leaves (bottom) of 'White Moon'. Foliage and floret colors in the photographs may appear different from the actual colors due to light reflectance.

DETAILED BOTANICAL DESCRIPTION

The following observations, measurements and values describe an one-gallon container with three plants of the new cultivar grown in Bonsall, Calif., under outdoor, full-sun conditions with day temperatures ranging from 18 to 35° C. and night temperatures ranging from 13 to 18° C.

Color references are made to The Royal Horticultural Society Colour Chart except where general terms of ordinary dictionary significance are used.

Botanical classification: *Osteospermum ecklonis* cultivar 'White Moon'.

Parentage:

*Female, or seed, parent.*—Proprietary selection of *Osteospermum ecklonis* identified as 90/75.

*Male, or pollen, parent.*—*Osteospermum ecklonis* cultivar Sparkler II, not patented.

Propagation:

*Type.*—By terminal cuttings and by tissue culture.

*Time to initiate roots.*—About 14 days at 22° C.

*Time to develop roots.*—About 20 days 22° C.

*Rooting habit.*—Fine to thick; freely branching.

Plant description:

*Appearance.*—Perennial herbaceous container and garden plant. Very broad inverted triangle. Upright, mounding and outwardly spreading growth habit. Dense foliage and erect flower stems. Freely branching with about 7 lateral branches; removal of terminal apices (pinching) will enhance branching.

*Crop time.*—About 8 to 12 weeks are required to produce a finished, flowering plant in a 10-cm container.

*Vigor.*—Vigorous.

*Plant height.*—About 30 cm.

*Plant spread.*—About 26 cm.

*Lateral branch description.*—Length: About 28 to 30 cm. Diameter: About 5 mm. Internode length: About 8 to 10 mm. Texture: Glabrous; stems thick and somewhat succulent. Color: 144B to 144C.

*Foliage description.*—Leaves alternate, single. Quantity of leaves per lateral branch: Numerous, about 30. Length, fully expanded leaves, basal: About 4.5 cm. Width, fully expanded leaves, basal: About 2 to 2.5 cm. Shape: Elliptic with irregular points along margin. Apex: Broadly acute. Base: Attenuate, sessile. Margin: Entire with widely-spaced teeth. Aspect: Undulate. Texture: Leathery, rough. Color: Young foliage, upper surface: 143A. Young foliage, lower surface: 143C. Fully expanded foliage, upper surface: 146A. Fully expanded foliage, lower surface: 146B. Attenuated leaf base: 144B. Venation, upper surface: 146B. Venation, under surface: 146C.

Inflorescence description:

*Appearance.*—Daisy-type composite inflorescence form. Inflorescences displayed above foliage, upright on long peduncles arising from leaf axils. Disc and ray florets arranged acropetally on a capitulum. Typically about 11 opened inflorescences per plant. Inflorescences last about one week. New inflorescences bypass older inflorescences. Inflorescences persistent.

*Flowering response.*—Plants flower continuously from April to October in the Northern Hemisphere.

*Fragrance.*—None detected.

*Inflorescence size.*—Diameter: About 7.5 cm. Depth (height): About 1.3 cm. Diameter of disc: About 1.1 cm.

*Inflorescence buds.*—Length: About 1.3 cm. Width: About 9 mm. Shape: Ovoid. Color: 145C.

*Ray florets.*—Quantity of ray florets per inflorescence: About 18 in a single whorl. Length: About 3.8 cm. Width: About 8 mm. Shape: Ligulate. Apex: Tridentate, minute. Base: Attenuate. Margin: Entire. Aspect: Nearly flat. Texture: Smooth, satiny. Color: When opening, upper surface: 155D. When opening, lower surface: 155A with fine stripes, 189B. Fully opened, upper surface: 155C/155D with faint blue, 98C, at base. Fully opened, under surface: 155A with stripes, 189B.

*Disc florets.*—Quantity of disc florets per inflorescence: Numerous, about 74. Shape: Tubular to salverform; five-lobed, fluted at apex. Length: About 6 mm. Width: About 2 mm. Color: Immature: 157A; apices, 98A/98B. Mature: 157A; apices, 98B.

*Phyllaries.*—Quantity per inflorescence and arrangement: About 18 per inflorescence; single whorl, fused at base. Length: About 1.2 cm. Shape: Linear. Apex: Narrowly acute. Margin: Entire. Texture: Slightly coarse. Color: Upper surface: 138B. Lower surface: 138A.

*Peduncle.*—Length: About 7 to 9.5 cm. Aspect: Moderately strong, inflorescences held erect above foliage. Texture: Smooth. Color: 145B.

*Reproductive organs.*—Androecium: Present on disc florets only. Stamens: Five. Anther shape: Oblong. Anther size: About 1.5 mm. Anther color: 102A. Pollen: Scarce. Pollen color: 17A. Gynoecium: Present on ray and disc florets. Pistils: One. Pistil length: About 0.5 mm. Stigma shape: Bipartite. Stigma color: 103B. Style length: About 6 mm. Style color: 155D. Ovary color: 145A.

Disease resistance: Resistance to pathogens common to Osteospermum has not been observed.

Seed production: Seed production has not been observed.

It is claimed:

1. A new and distinct cultivar of Osteospermum plant named 'White Moon', as illustrated and described.

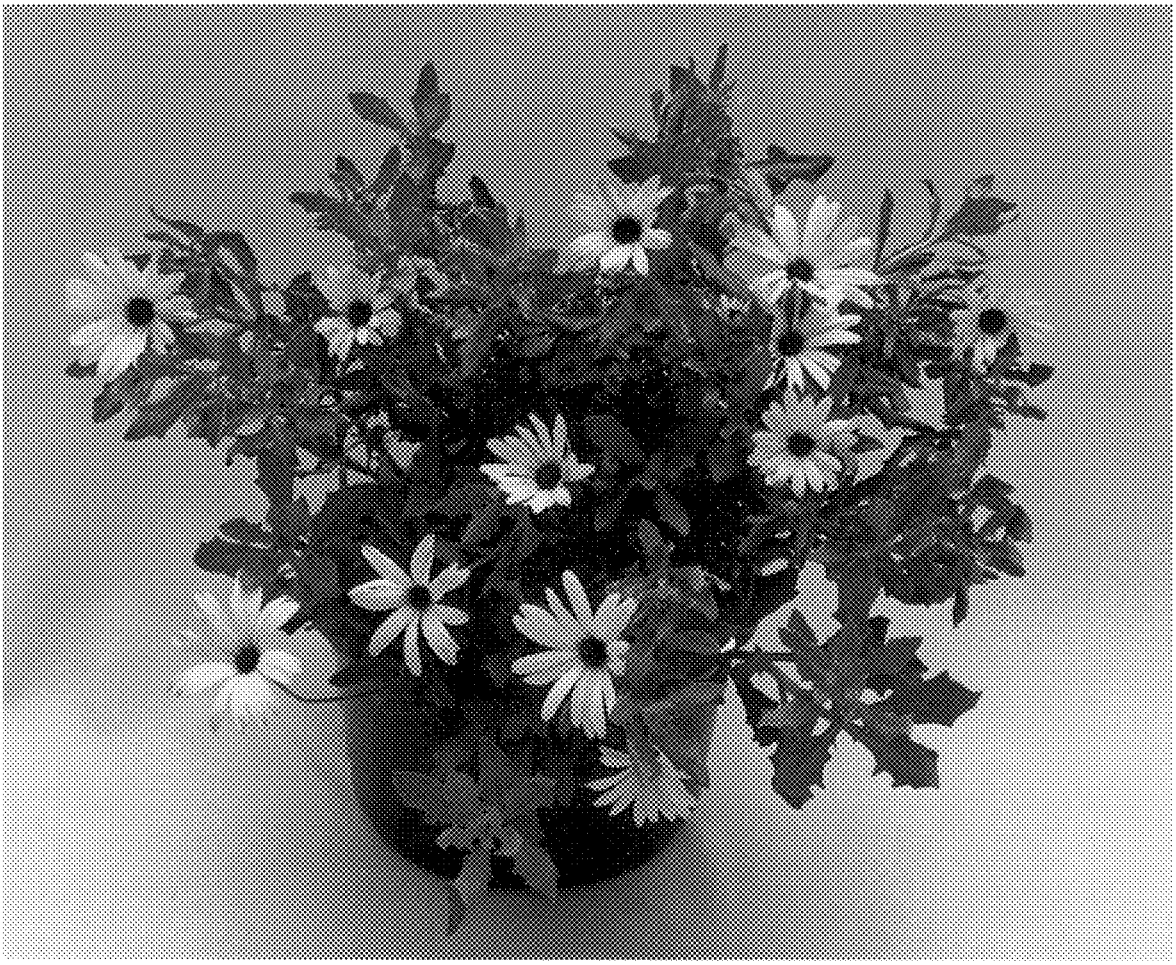
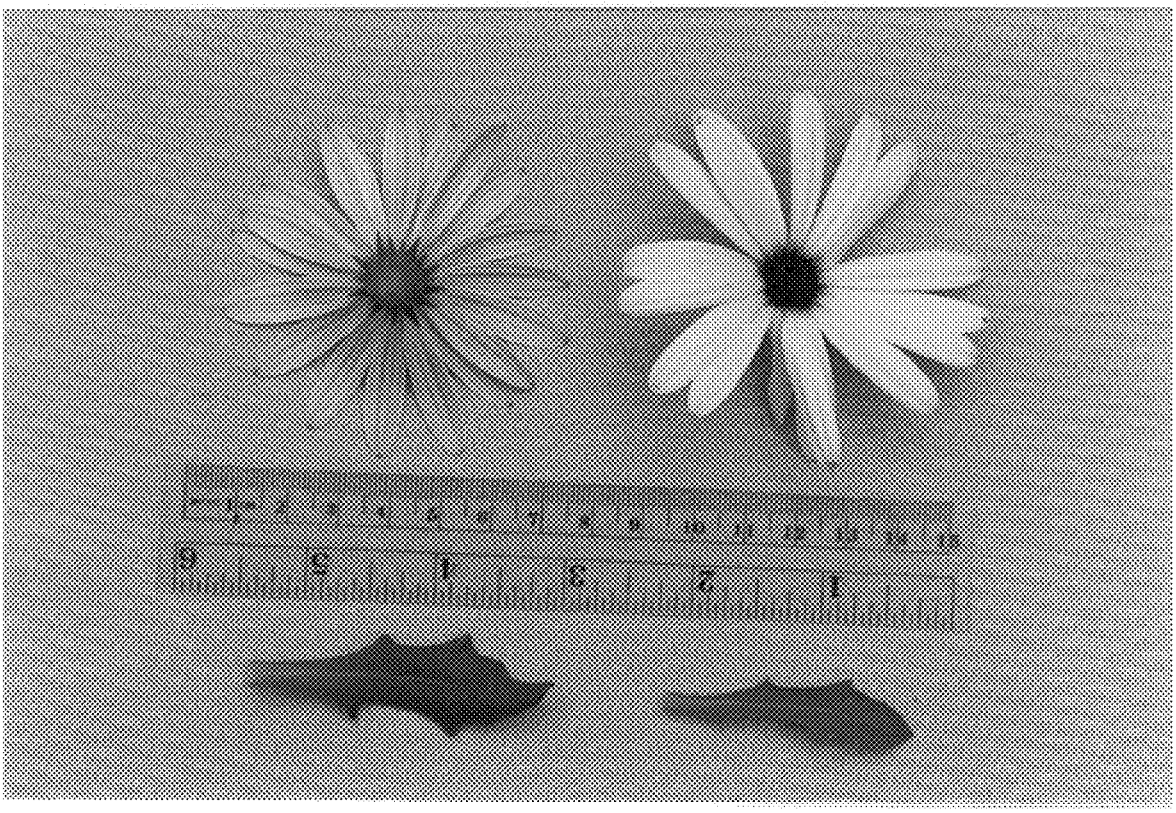

* * * * *